United States Patent [19]

Binder

[11] Patent Number: 4,586,929
[45] Date of Patent: May 6, 1986

[54] HYDROGEL KERATOPROSTHESIS

[76] Inventor: Perry S. Binder, P.O. Box 1097, Rancho Santa Fe, Calif. 92067

[21] Appl. No.: 597,733

[22] Filed: Apr. 6, 1984

[51] Int. Cl.⁴ .............................................. A61F 2/14
[52] U.S. Cl. ...................................................... 623/5
[58] Field of Search ............................................. 3/13

[56] References Cited

U.S. PATENT DOCUMENTS

| 3,458,870 | 8/1969 | Stove, Jr. | 3/13 |
| 3,679,504 | 7/1972 | Wichterle | 3/13 |
| 4,470,159 | 9/1984 | Peyman | 3/13 |

OTHER PUBLICATIONS

Present Status of Prosthokeratoplasty; Ramon Castoviejo, MD, Hernando Cardona, MD, and A. Gerard DeVoe, MD; *American Journal of Ophthalmology*, vol. 68, No. 4, Oct., 1969.
Keratoprosthesis; James V. Aquavella, MD, Gullapalli N. Rao, MD, Alan C. Brown, MD, and Jeffrey K. Harris, MD; *Ophthalmology*, vol. 89, No. 6, Jun., 1982.
Biology of Complications Following Keratoprosthesis; C. H. Dohlman, *Cornea*, vol. 2, pp. 175–176, 1983.
Keratoprosthesis; L. J. Girard, *Cornea*, vol. 2, pp. 207–224, 1983.
Ceramic Keratoprosthesis: Biomechanics of Extrusion in Thru-The-Lid Implantation; *Cornea*, vol. 2, pp. 197–201, 1983.
Hydrogel Keratophakia in Non-Human Primates; Binder, P. S., Deg, J. K., and Zavala, E. Y. *Current Eye Res.*, 1:535, 1982.
Hydrogel Implants for the Correction of Myopia; Binder, P. S., *Current Eye Res.*, 2:7 1982/1983.
Hydrophilic Lenses for Refractive Keratoplasty; The Use of Factory Lathed Materials, Binder, P. S., Baumgartner, S. D., Deg, J. K., Zavala, E. Y., *Clao Journal*, 10:105, 1984.
Hydrogel Refractive Keratoplasty; Lens Removal and Exchanges, Binder, P. S., Zavala, E. Y., Deg, J. K., *Cornea* 2:119, 1984.
Morphology of Hydrogel Implants Used for Refractive Keratoplasty; Samples, J. R., Binder, P. S., Baumgartner, S. D. *Invest Ophthalmol Vis. Sci.*, 25:843, 1984.
Alloplastic Corneal Implants for the Correction of Refractive Errors, Binder P. S., Zavala, E. Y., Baumgartner, S. D., Deg, J. K. *Ophthalmology*, 91:806, 1984.
Ceramic Keratoprosthesis; Polack, F. M., MD, Gunther, H., PhD., *Ophthalmology*, vol. 87, No. 7, Jul., 1980, pp. 693–697.

*Primary Examiner*—Mark L. Bell
*Attorney, Agent, or Firm*—Lyon & Lyon

[57] ABSTRACT

A device which may be implanted in the cornea of the eye to replace both the cornea and the lens, and which is biocompatible with the tissue in the eye. A concave base plate with a support cylinder connected integrally through its center is used and implanted in the eye using a microkeratome technique. An optical cylinder with threads formed about its periphery is screwed into the support cylinder to focus the light in the eye. The base plate and support cylinder are made of a hydrogel material having a water content ranging from 30 percent to 79 percent which is biocompatible with the tissue in the eye.

14 Claims, 6 Drawing Figures

HYDROGEL KERATOPROSTHESIS

BACKGROUND OF THE INVENTION

The field of the invention is artificial corneas and lenses, and more particularly, through-and-through keratoprostheses.

The front of the eye is covered by the cornea. The cornea refracts light through the anterior chamber and into the lens area of the eye. In the lens area of the eye, muscles control the size of the entrance aperture of the eye, also known as the pupil. The lens is suspended in this area and focuses the refracted light through the vitreous chamber and onto the retina in the back of the eye. The shape of the lens can be varied by muscles within the eye to focus on objects that are close or far away.

Often, irregularity in vision is created by problems with the cornea and/or the lens. In addition, many people have severe corneal disorders caused by accidents. For example, millions of people are unable to see due to severe dry eye conditions, alkali explosions, traumatic lacerations, or other accidents wherein acid or some other such chemical has come into contact with the surface of the eye. Such accidents usually produce permanent opacity in the cornea and lens of the eye. Some patients having occular chemical burns may receive corneal transplant surgery using donor human corneal material to replace the scarred, opaque cornea. In the overwhelming majority of the chemical burn cases, however, this is not possible due to the shortage of such donor material, rejection by the recipient's body and most importantly, the presence of an abnormal ocular surface and dry eye syndrome which usually remains after ocular surface burns; the last two of which reduce the chances of successful corneal transplantation to less than 1 in 5.

In order to solve this problem, the medical community has attempted to develop a variety of artificial devices which may be used in place of a corneal transplant. One such device is known as a keratoprosthesis. There are essentially two types of keratoprostheses; the "nut and bolt" keratoprosthesis and the "through-and-through" keratoprosthesis.

The nut and bolt keratoprosthesis involves surgically implanting a cylinder into the eye and using a nut made from some synthetic material and positioned on the back side of the cornea to secure the cylinder. The cylinder then acts as both the lens and the cornea to focus light onto the retina. While using a similar optical cylinder, the concept of the through-and-through keratoprosthesis involves surgically implanting a base plate within the cornea to support the optical cylinder.

While the idea behind a keratoprothesis has existed for a long time, the major problem has been in making a successful keratoprosthesis out of a biocompatible material. The major reasons for failure of presently used keratoprostheses are related to the bioincompatibility of the materials which produce wound leaks, ocular infections and extrusion of the keratoprosthesis from the eye.

SUMMARY OF THE INVENTION

Applicant's experiments have shown that hydrogel material having a water content of 30% to 79% (hereinafter hydrogel) is biocompatible with the cornea and will support construction of a biocompatible keratoprosthesis. In addition, use of applicant's design and procedure has been successful in avoiding ocular infections, post-operative wound leaks and extrusion of the hydrogel material from the cornea. Such a hydrogel keratoprosthesis will enable millions of blind people to have their vision restored as a result of surgery using the artificial device.

In a preferred embodiment of the present invention a hydrogel base plate, which is substantially concave, is surgically implanted in the cornea using a microkeratome technique. A support cylinder is integrally formed through the center of the base plate and protrudes from each side of the base plate, perpendicular to the surface thereof, and through an opening cut in the cornea. The support cylinder has threads formed about its interior. An optical cylinder with threads formed about its periphery is screwed into the hydrogel support cylinder and base plate. The edges of the base plate are rounded to prevent tearing of the base plate and irritation of the corneal tissue. The base plate is sufficiently large and concave in shape to avoid post-operative extrusion through the surgical wound. The base plate is sutured in place within the cornea. The excised part of the cornea is placed over the baseplate-support cylinder combination and sutured in place.

An object of the invention is to provide an improved artificial supporting device which may be surgically implanted in the cornea and is biocompatible with the cornea.

A further object of the invention is to provide keratoprosthesis of readily available material to avoid problems of extreme tissue shortage such as exists with donor human material.

A further object of the invention is to provide a keratoprosthesis for persons who medically require eye surgery in order to regain their vision which will not be extruded from the eye, tend not to promote ocular infections and help prevent leaking from the surgical wound. Other and more detailed objects of the invention will become apparent upon examination of the drawings and description herein.

DETAILED DESCRIPTION OF THE INVENTION

Figure 1:
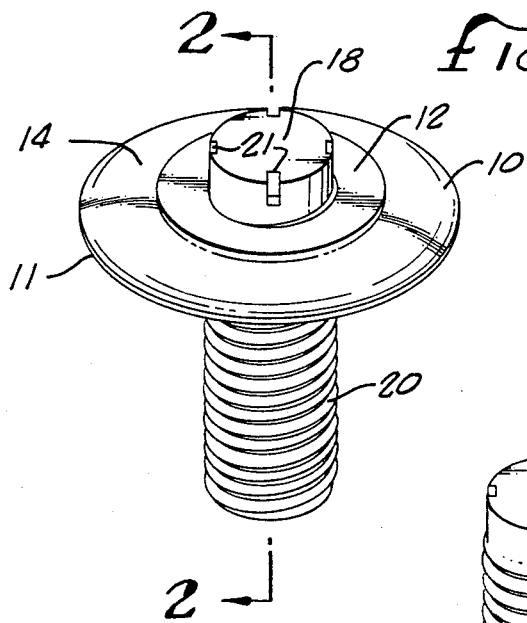
FIG. 1 is a perspective view of the assembled keratoprosthesis.
Figure 2:
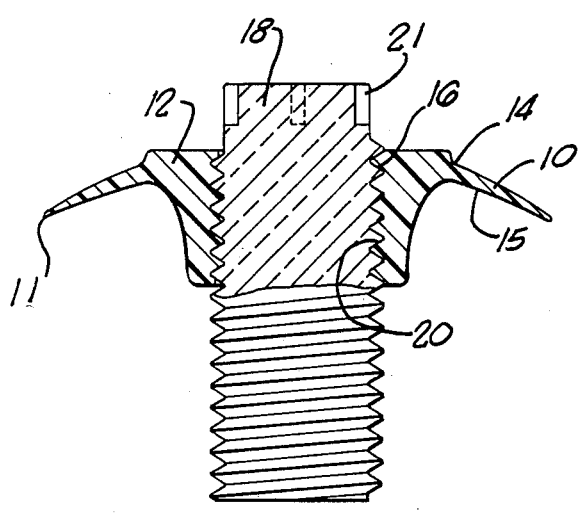
FIG. 2 is a cross-sectional view taken substantially along the line 2—2, of FIG. 1.
Figure 3:
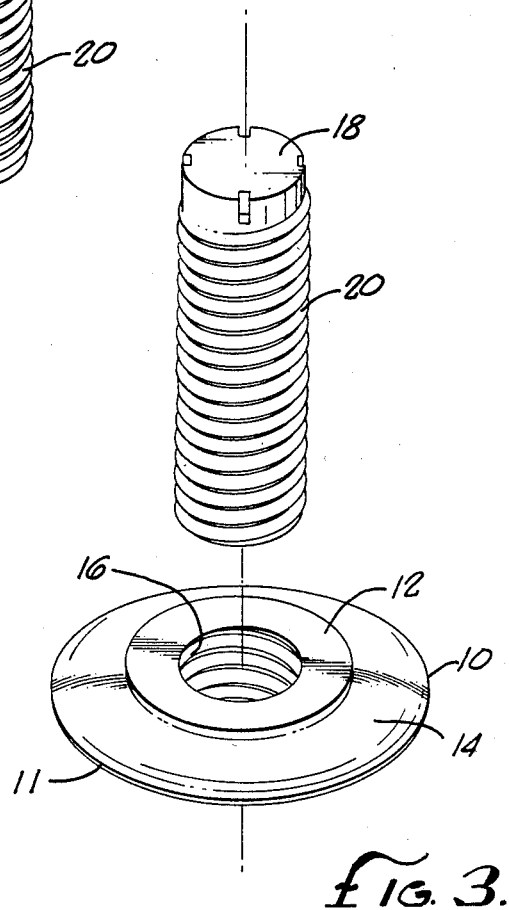
FIG. 3 is a perspective view of the unassembled keratoprosthesis.

As shown in FIGS. 1-3, a preferred embodiment of the invention is designed to be surgically implanted into the cornea of the eye 8. The keratoprosthesis has a base plate 10 which is substantially concave and has a rounded circumferential edge 11. A support cylinder 12 is integrally formed through the center of the base plate 10. The support cylinder 12 protrudes through, and is perpendicular to, the top face 14 and the bottom face 15 of the base plate 10. Threads 16 are formed about the inside of the support cylinder 12.

The base plate 10 and the support cylinder 12 are constructed from a hydrogel material having a water content ranging from 30% to 79% (hereinafter hydrogel). Applicant has found that such hydrogen material will support construction of the above described components as described hereinafter and still be biocompatible with the eye.

Referring to the figures, an optical cylinder 18 has threads 20 formed about its periphery along all but a small portion of its longitudinal axis. The optical cylinder 18 is typically made of polymethyl methacrylate but may be made from some other suitable material including hydrogel. The threads 16 and 20 form inclined engagement surfaces. The optical cylinder 18 has small notches 21 formed in the end which protrudes outward from the eye 8 in order to facilitate screw adjustment of the optical correction provided by the keratoprosthesis. While the outer surface of the optical cylinder 10 may be colored to enable easy visualization of the cylinder 18 the internal portion of the cylinder should be clear to enable the patient to see.

The keratoprosthesis is implanted into the eye as follows. A lamellar keratectomy is performed either with a not-shown microkeratone or free-hand, as is known to those skilled in the art of refractive corneal surgery, so that a layer 28 of corneal tissue is removed (keratectomized). The keratectomized portion 28 should have an outer diameter of at least 8.5 mm and a thickness of 0.2 mm to 0.25 mm. A not-shown trephine is used to cut a hole 22 through the center of the remaining host cornea 24 to accommodate the support cylinder 12. This hole 22 should be slightly smaller than the outer diameter of the support cylinder 12 so as to maintain the position of the support cylinder 12. The base plate 10 and support cylinder 12 are then implanted onto the surface 25 of the remaining host cornea 24 and sutured 26 in at least three places to maintain their position.

Figure 4:
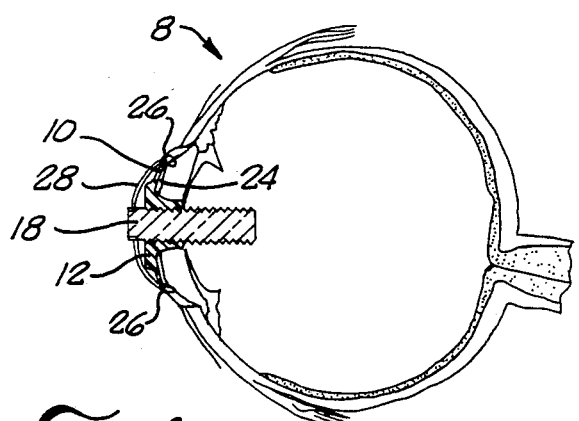
FIG. 4 is a partially cross-sectional view showing the keratoprosthesis implanted in an eye.
Figure 6:
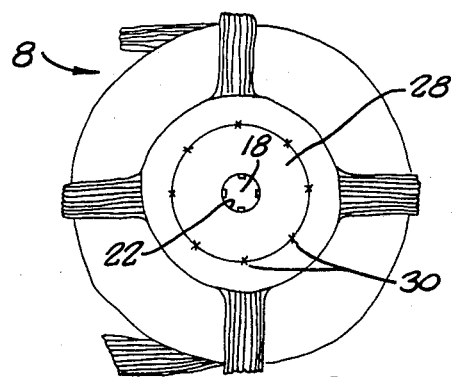
FIG. 6 is a front view showing the keratoprosthesis implanted in an eye without the eyelid being sutured closed.
Figure 5:
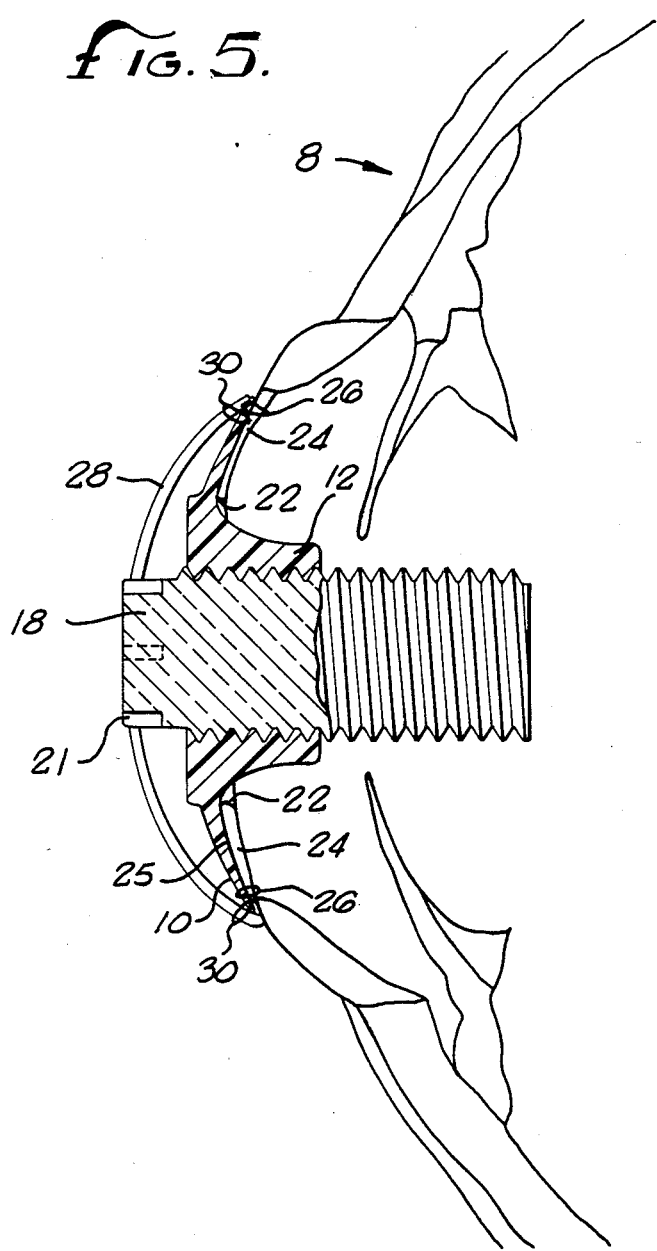
FIG. 5 is an enlargement of the relevant portion of the device implanted in the cornea as shown in FIG. 4.

The keratectomized portion 28 of the cornea is also trephined, so as to have a corresponding hole 22a in its center to accommodate the protruding support cylinder 12 and optical cylinder 18. The keratectomized corneal tissue 28 is then positioned above the base plate 10 and support cylinder 12 and sutured 30 into place as shown in FIGS. 4–6 with 8 to 16 monofilament nylon sutures which may or may not be buried. The optical cylinder 18 is inserted into the support cylinder 12 so that its position is retained by the coaction of the threads 16 and 20.

The entire corneal surface is covered with pretibial periostium or similar material. If sufficient conjunctiva is available, it will be used to overlie the pretibial periostium. In severe dry eye cases, it may be necessary to excise the tarsal conjunctiva and the tarsus and orbicularis muscle so that the eyelid may be sutured closed over the keratoprosthesis. An incision can be made at a later date made through the eyelid to allow the notched end of the optical cylinder 18 to protrude through the eyelid. A not-shown tool is used to adjust the correction provided by the optical cylinder by screwing the cylinder 18 in or out of the base plate 10 and support cylinder 12. As such, the optical cylinder 18 functions as both a cornea and a lens for the damaged eye 8.

We claim:

1. A keratoprosthesis, comprising,
   a substantially concave hydrogel base plate including a substantially centrally disposed support cylinder integrally fitted through said base plate, said support cylinder protruding through at least one side of said base plate,
   inclined engagement surfaces formed within said support cylinder, and
   an optical cylinder with inclined engagement surfaces formed about its periphery for engagement with said support cylinder.

2. A keratoprosthesis as set forth in claim 1 wherein said hydrogel has a water content ranging from 30 percent to 79 percent.

3. A keratoprosthesis with a polymethylmethacrylate or hydrogel optical cylinder, comprising, a hydrogel base plate with an integral support cylinder formed therethrough, said hydrogel having a water content ranging from 30 percent to 79 percent, and retaining means to retain the optical cylinder within said support cylinder.

4. The keratoprosthesis as set forth in claim 3 wherein said base plate is substantially concave and said support cylinder is formed perpendicular to said base plate.

5. A keratoprosthesis as set forth in claim 4 wherein said retaining means are threads formed about the periphery of the optical cylinder and about the interior of said support cylinder.

6. The keratoprosthesis as set forth in claim 4 wherein the circumferential edge of said base plate is substantially rounded.

7. A keratoprosthesis, comprising, a concave hydrogel base plate with a rounded circumferential edge, said hydrogel having a water content ranging from 30 percent to 79 percent, a support cylinder formed integrally with said base plate and protruding perpendicular through the center of said base plate, an optical cylinder fitted within said support cylinder and means to retain said optical cylinder within said support cylinder.

8. A keratoprosthesis as set forth in claim 7 wherein the external surface of said optical cylinder is colored.

9. The keratoprosthesis as set forth in claim 7 wherein inclined engagement surfaces are used to retain said optical cylinder within said support cylinder.

10. A method of correcting visual disorders, the steps comprising,
    removing the outer layer of scarred corneal tissue from eye,
    cutting a hole through the center of the remaining cornea to accommodate a keratoprosthesis,
    implanting a hydrogel keratoprosthesis onto the surface of the remaining cornea and securing it in place with at least one suture, said hydrogel keratoprosthesis including a base plate formed from a hydrogel material, said base plate having a support cylinder formed integrally therethrough,
    centrally trephining the excised portion of the cornea to accomodate the keratoprosthesis,
    suturing the removed corneal tissue over the keratoprosthesis to secure it in the eye,
    suturing the eyelid closed,
    making an incision through the eyelid to accommodate the optical cylinder, and
    adjusting the axial position of the optical cylinder within said support cylinder to provide the necessary optical correction.

11. The method as set forth in claim 10 wherein said hydrogel has a water content ranging from 30 percent to 79 percent.

12. The method as set forth in claim 11 wherein said outer layer of scarred corneal tissue is removed by using a microkeratome technique.

13. The method as set forth in claim 11 wherein said outer layer of scarred corneal tissue is removed by using a free-hand technique.

14. In a keratoprosthesis including an optical cylinder with inclined engagement surfaces formed about its periphery, the improvement comprising a hydrogel base plate including a substantially centrally disposed integrally connected support cylinder through said base plate, said support cylinder protruding through at least one side of said base plate and inclined engagement surfaces formed about the inside periphery of said support cylinder along its longitudinal length, said base plate and support cylinder being arranged so as to maintain the optical cylinder at a preselected position upon engagement of the optical cylinder with said inclined surfaces of said support cylinder.

* * * * *